(12) United States Patent
Steeger et al.

(10) Patent No.: US 8,265,555 B2
(45) Date of Patent: Sep. 11, 2012

(54) TUBE NOZZLE FOR A RESPIRATOR

(75) Inventors: Markus Steeger, Lübeck (DE); Mark Oliver Gertz, Lübeck (DE); Gerd Wotha, Warnstorf (DE)

(73) Assignee: Dräger Medical GmbH, Lübeck (DE)

( * ) Notice: Subject to any disclaimer, the term of this patent is extended or adjusted under 35 U.S.C. 154(b) by 478 days.

(21) Appl. No.: 12/621,861

(22) Filed: Nov. 19, 2009

(65) Prior Publication Data

US 2010/0151785 A1 Jun. 17, 2010

(30) Foreign Application Priority Data

Dec. 16, 2008 (DE) .......................... 10 2008 062 319

(51) Int. Cl.
*H04B 5/00* (2006.01)

(52) U.S. Cl. ................... 455/41.1; 455/41.2; 455/193.2; 607/61

(58) Field of Classification Search ................. 455/41.1, 455/41.2, 193.2, 319, 292, 318, 197.2; 607/61, 607/33, 116; 600/410, 423
See application file for complete search history.

(56) References Cited

U.S. PATENT DOCUMENTS

| | | | | |
|---|---|---|---|---|
| 4,237,900 A | * | 12/1980 | Schulman et al. | 600/301 |
| 5,264,843 A | * | 11/1993 | Silvian | 340/870.18 |
| 6,126,610 A | | 10/2000 | Rich et al. | |
| 6,178,353 B1 | * | 1/2001 | Griffith et al. | 607/61 |
| 7,009,511 B2 | * | 3/2006 | Mazar et al. | 340/531 |
| 7,060,030 B2 | * | 6/2006 | Von Arx et al. | 600/300 |
| 7,292,139 B2 | * | 11/2007 | Mazar et al. | 340/531 |
| 7,668,596 B2 | * | 2/2010 | Von Arx et al. | 607/32 |
| 7,749,194 B2 | * | 7/2010 | Edwards et al. | 604/131 |
| 8,049,489 B2 | * | 11/2011 | Gauglitz et al. | 324/207.16 |
| 8,140,168 B2 | * | 3/2012 | Olson et al. | 607/61 |
| 2003/0032993 A1 | | 2/2003 | Mickle et al. | |
| 2004/0117204 A1 | * | 6/2004 | Mazar et al. | 705/2 |
| 2006/0191354 A1 | | 8/2006 | Schulz et al. | |
| 2007/0156042 A1 | * | 7/2007 | Unal | 600/410 |
| 2007/0265877 A1 | | 11/2007 | Rice et al. | |
| 2008/0090595 A1 | * | 4/2008 | Liu et al. | 455/461 |
| 2008/0119919 A1 | * | 5/2008 | Atalar et al. | 607/116 |
| 2008/0173308 A1 | | 7/2008 | Schermeier et al. | |
| 2008/0200776 A1 | | 8/2008 | Schermeier et al. | |
| 2008/0255782 A1 | * | 10/2008 | Bilac et al. | 702/62 |

(Continued)

FOREIGN PATENT DOCUMENTS

EP 1 579 884 A1 9/2005

(Continued)

*Primary Examiner* — Minh D Dao
(74) *Attorney, Agent, or Firm* — McGlew & Tuttle, P.C.

(57) ABSTRACT

A coupling device (1) is provided, especially a tube nozzle (2), for a medical device (3), especially a respirator (4), for the mechanical and electromagnetic coupling of the medical device (3) with the accessory (6), especially a tube system (19). The device includes a mechanical device for coupling the medical device (3) with the accessory (6), at least one inductance (8), at least one capacitance (12) and at least one electric line (18) for forming an electric circuit as a resonant circuit for the electromagnetic coupling of an inductance (8) at the medical device (3) with an inductance (8) at the accessory (6). The coupling device (1) is able to be checked for trouble-free operation without the accessory (6). The coupling device (1) is able to be manufactured at a low cost and make safe and reliable handling possible. The coupling device (1) has a semiconductor chip (16) for storing and/or processing at least one piece of information and/or for sending and/or receiving at least one signal.

16 Claims, 2 Drawing Sheets

U.S. PATENT DOCUMENTS

| | | | |
|---|---|---|---|
| 2008/0313486 A1* | 12/2008 | Parfitt | 713/600 |
| 2009/0084586 A1* | 4/2009 | Nielsen | 174/255 |
| 2010/0174348 A1* | 7/2010 | Bulkes et al. | 607/116 |
| 2010/0318160 A1* | 12/2010 | Stevenson et al. | 607/63 |
| 2011/0196229 A1* | 8/2011 | Weiss et al. | 600/423 |
| 2011/0218622 A1* | 9/2011 | Shaolian et al. | 623/2.37 |
| 2011/0306860 A1* | 12/2011 | Halperin et al. | 600/372 |
| 2012/0092775 A1* | 4/2012 | Duston et al. | 359/666 |
| 2012/0109273 A1* | 5/2012 | Doan et al. | 607/116 |

FOREIGN PATENT DOCUMENTS

| | | |
|---|---|---|
| EP | 1 731 188 A2 | 12/2006 |
| EP | 1 852 810 A1 | 11/2007 |

\* cited by examiner

TUBE NOZZLE FOR A RESPIRATOR

CROSS REFERENCE TO RELATED APPLICATIONS

This application claims the benefit of priority under 35 U.S.C. §119 of German Patent Application DE 10 2008 062 319.9 filed Dec. 16, 2008, the entire contents of which are incorporated herein by reference.

FIELD OF THE INVENTION

The present invention pertains to a coupling device for a medical device for the mechanical and electromagnetic coupling of the medical device with an accessory, and to a system with a medical device, with an accessory and with a coupling device for mechanically and electromagnetically coupling the medical device with the accessory and to a process for detecting a state of a coupling device, especially a tube nozzle, for mechanically and electromagnetically coupling a medical device, especially a respirator, with the accessory, especially a tube system and/or process for checking a communication between the medical device and the accessory.

BACKGROUND OF THE INVENTION

Respirators (also known as ventilators) as medical devices are used for the artificial respiration of patients. The respirator is connected by means of a tube nozzle to a tube system as an accessory. The air is sent through the tube system to the patient for artificially respirating the patient. The tube nozzle as a coupling device is used to mechanically couple the respirator to the tube system or vice versa in a fluid-tight manner. An induction coil as an RFID antenna and a writing and/or reading module are installed in the respirator. An inductance, a capacitance and a semiconductor chip are integrated in the tube system to form an RFID transponder. The tube system thus comprises an electric resonant circuit with a semiconductor chip. The tube nozzle is provided with an inductance, a capacitance and an electric conductor for forming a resonant circuit. When sending electromagnetic waves or a magnetic wave from the induction coil of the respirator, the resonant circuit in the induction coil is set to resonate, so that a magnetic field is also sent by the resonant circuit in the tube nozzle and this magnetic field is passed on to the tube system. The distance between the inductance or induction coil in the respirator and the inductance in the tube system can be bridged over in this manner. Information, for example, treatment parameters of the patient, parameters for reprocessing the tube system or other technical parameters are contained in the semiconductor chip of the tube system. The respirator is connected to different tube systems, so that transmission of information or data from the respirator to the tube system and vice versa is necessary. This takes place in a wireless manner between the RFID transponder in the tube system with the inductance, the capacitance and the semiconductor chip and the writing and/or reading module in the respirator and vice versa.

The tube nozzles are to be cleaned and disinfected by means of autoclaving at regular intervals. The tube nozzles may be damaged when they are being treated in the autoclave. So-called service transponders are arranged in the immediate vicinity of the respirator within the framework of a continuous and initial self-test. The respirator checks the function of the RFID writing and/or reading module and of the induction coil in the respirator by means of the service transponders. Furthermore, it is necessary for checking the operatability of the tube system.

SUMMARY OF THE INVENTION

The object of the present invention is therefore to make available a coupling device, a system and a process, in which the coupling device can be checked for trouble-free action without the accessory. The coupling device and the system shall be manufactured cost-effectively and they shall make safe and reliable handling possible.

This object is accomplished with a coupling device, especially a tube nozzle, for a medical device, especially a respirator or a device for supplying drugs, for the mechanical and/or fluid-tight and electromagnetic coupling of the medical device with an accessory, especially with a tube system or with a tube, comprising a mechanical means for mechanically coupling the medical device with the accessory, at least one inductance, at least one capacitance and at least one electric line for forming an electric circuit as a resonant circuit for electromagnetically coupling an inductance at the medical device with an inductance at the accessory, wherein the coupling device comprises a semiconductor chip for storing and/or processing at least one piece of information and/or for sending and/or receiving at least one signal.

In addition, a semiconductor chip is installed in the coupling device. The semiconductor chip can store and/or process information or send and/or receive signals. The signals may contain information or data. The sending and receiving is transmitted by means of electromagnetic waves. It is not absolutely necessary for the coupling device to send an electromagnetic field itself for sending signals, but an electromagnetic sending field of the medical device or of the accessory may be changed as well.

In particular, the semiconductor chip is an RFID semiconductor chip and/or the coupling device is an RFID transponder or the coupling device has the function of an RFID transponder.

In another embodiment, the coupling device has a first inductance to be arranged in the area of the medical device and a second inductance to be arranged in the area of the accessory. A current is induced as a magnetic field in the first inductance by means of the magnetic waves sent by the medical device and magnetic waves are sent by the second inductance. The first and second inductances are preferably designed as induction coils each. The first and second inductances are connected by means of an electrical line to a capacitance and form an electrical resonant circuit as an electrical oscillating circuit.

In an additional embodiment, the semiconductor chip is electrically connected by means of two capacitances to the first electric circuit as a resonant circuit to supply the semiconductor chip with electric energy. Thus, it is a passive RFID transponder, which draws its energy from the radio waves received. In another embodiment, it may also be an active RFID, so that an electric storage unit is integrated in the coupling device.

The semiconductor chip, an inductance and at least one electric line preferably form a second electric circuit as a resonant circuit.

In one variant, the coupling device is designed as a tube nozzle. For example, a medical device, designed as a respirator, is connected to the tube system by means of the tube nozzle. The tube nozzle is attached both to a port at the medical device and to the tube system, i.e., to an end of a tube. It is, in general, necessary to couple two tubes to the respirator and to connect them, in a fluid-tight manner separately from one another, to the respirator. They are an expiration tube and an inspiration tube.

The medical device is preferably a respirator and/or the accessory is a tube system.

A system according to the present invention with a medical device, an accessory and a coupling device for the mechanical and electromagnetic and/or fluid-tight coupling of the medical device with the accessory, wherein the medical device comprises an inductance for generating an electromagnetic field and a writing and/or reading module, the accessory comprises at least one inductance, preferably at least one capacitance, preferably at least one electric line and a semiconductor chip, and the coupling device comprises a mechanical means for mechanically coupling the medical device with the accessory, at least one inductance, at least one capacitance and at least one electric line for forming an electric circuit as a resonant circuit for electromagnetically coupling the inductance at the medical device with the inductance at the accessory, wherein the coupling device is designed according to a coupling device described in this application.

In another embodiment, the electric operatability of the coupling device, especially of the tube nozzle, can be detected by the medical device by means of the semiconductor chip in the coupling device in another embodiment.

The writing and/or reading module preferably comprises a semiconductor chip and can store and/or process and/or send and/or receive information and/or signals. For example, it is part of the control of the medical device or it is the control of the medical device.

In particular, the operatability of a communication between the medical device and the accessory, especially tube systems, can be detected by the medical device by means of the semiconductor chip in the coupling device.

Process according to the present invention for detecting a state of an accessory for the mechanical and electromagnetic coupling of a medical device with the accessory and/or process for checking a communication between the medical device and the accessory, especially for a system described in this application, with the steps: Sending an electromagnetic field from the medical device, induction of electric current in a resonant circuit as an electric circuit with at least one inductance, at least one capacitance and at least one electric line in the coupling device by means of energy from the magnetic field of the medical device, sending of a magnetic field by means of the resonant circuit in the coupling device, induction of electric current in a resonant circuit as an electric circuit with at least one inductance, at least one capacitance and at least one electric line with a semiconductor chip in the accessory, preferably sending of at least one piece of information and/or at least one signal from the medical device to the accessory and/or vice versa by means of the magnetic field, wherein at least one piece of information is stored and/or processed and/or at least one signal is received and/or sent by a semiconductor chip in the coupling device.

The at least one signal may contain, for example, information on the number of autoclaving operations. The signal or information may contain, furthermore, data, for example, for identifying the accessory, e.g., a lot number or a serial number, as well as data for supporting the medical device by stored information or data on compatibility between the accessory and the medical device as well as concerning technical parameters, e.g., also service data (number of autoclaving operations).

In an additional variant, the at least one piece of information and/or the at least one signal is transmitted in a wireless manner from the semiconductor chip with the resonant circuit in the coupling device to the medical device and/or vice versa by an electromagnetic field or magnetic field.

In another variant, at least one piece of information and/or at least one signal on the number of autoclaving cycles of the coupling device is stored in the semiconductor chip of the coupling device.

In another embodiment, the coupling device sends at least one signal, especially with an identification code concerning the coupling device and/or with at least one piece of information to the medical device after the magnetic field has been sent by the medical device, and the sending of the at least one signal to the medical device is interpreted to mean that trouble-free communication between the medical device and the coupling device and/or the accessory is possible and/or the coupling device is operative.

In particular, the coupling device sends no signal to the medical device after the magnetic field has been sent by the medical device, and the lack of sending of the signal to the medical device is interpreted to mean that trouble-free communication between the medical device and the coupling device and/or the accessory is not possible and/or the coupling device is not operative.

In general, the sending and/or receiving of a signal, e.g., with a piece of information or a control signal, by a semiconductor chip is controlled by the semiconductor chip and the physical, preferably wireless sending and/or receiving of the signal is performed by an inductance.

An exemplary embodiment of the present invention will be described in more detail below with reference to the attached drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
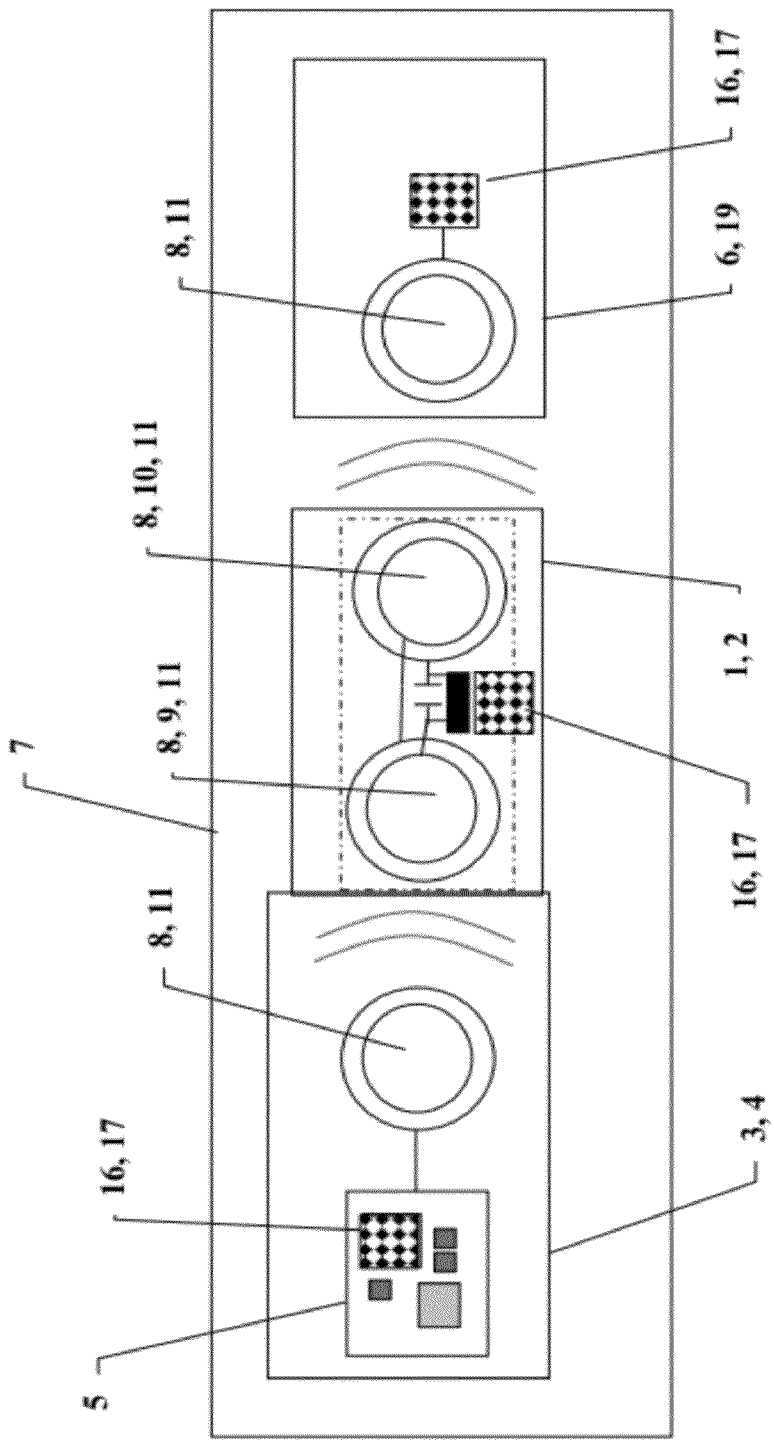
FIG. 1 is a highly schematic view of a system with a medical device, with an accessory and with a coupling device.

Referring to the drawings in particular, FIG. 1 shows a system 7 with an accessory 6 and with a coupling device 1 in a highly schematic form. The medical device 3 is a respirator 4 for artificially respirating patients. The coupling device 1 is a tube nozzle 2 for the mechanical, electromagnetic and fluid-tight coupling of the accessory 6 with the respirator 4. The accessory 6 is a tube system 19, which comprises an expiration tube and an inspiration tube as well as a Y-piece (not shown). An inductance 8, designed as an induction coil 11, is installed in the respirator 4. The induction coil 11 is connected to a writing and/or reading module 5 in the respirator 4. Alternating current is sent through the induction coil 11, so that a magnetic field is generated as an electromagnetic field by the induction coil 11.

Figure 2:
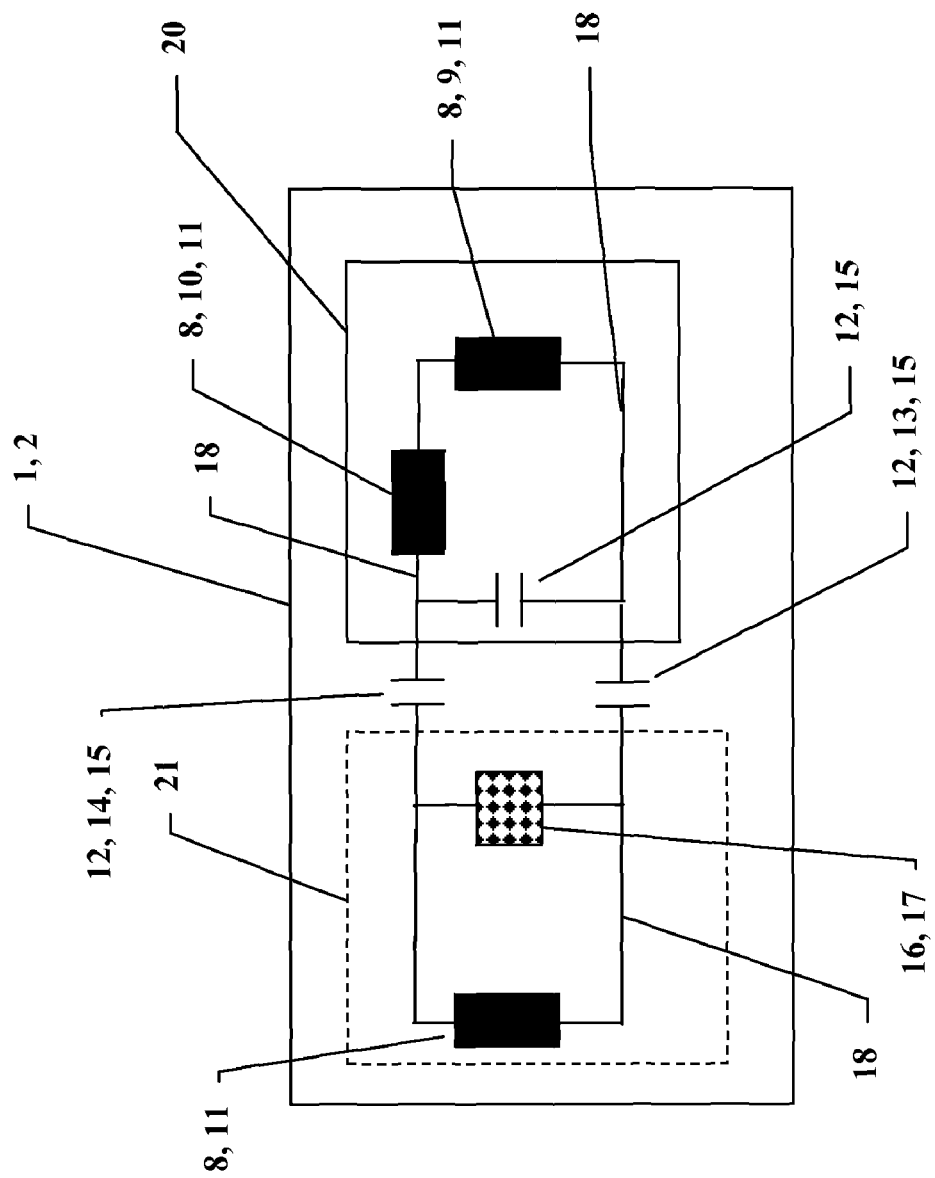
FIG. 2 is a schematic electric circuit diagram of the coupling device according to FIG. 1.

A first inductance 9 acting as an induction coil 11 and a second inductance 10 acting as an induction coil 11 are installed in the tube nozzle 2. Furthermore, a semiconductor chip 16, designed as an RFID semiconductor chip 17, is installed in the tube nozzle 2. The first and second inductances 9, 10 are connected to a capacitance 12 designed as a plate capacitor 15 by means of electric lines 18 (FIG. 2). The first and second inductances 9, 10 and the capacitance 12 thus form a first electric circuit 20 as a first electric oscillating circuit. A second electric circuit 21, acting as a second electric oscillating circuit or resonant circuit with the semiconductor chip 16 designed as an RFID semiconductor chip 17, is connected to said first electric oscillating circuit by means of a first capacitance 13 and a second capacitance 14, each designed as a plate capacitor 15. The second resonant circuit or electric oscillating circuit in the tube nozzle 2 is enclosed by a broken rectangular box in FIG. 2. The second resonant circuit can take up energy in the form of alternating voltage from the first resonant circuit by means of the first and second capacitances 13, 14 and thus supply the RFID semiconductor chip 17 with electric energy. The energy needed by the RFID semiconductor chip 17 hardly becomes noticeable in the first resonant circuit of the tube nozzle 2, so that sufficiently high voltages and currents are guaranteed there by the first and second inductances 9, 10 for a sufficiently wide transmission range from the respirator 4 to the tube system 19.

The electromagnetic waves sent as a magnetic field by the induction coil 11 in the respirator 4 induce an electric current in the first inductance 9 of the tube nozzle 2 in the area of the respirator 4. The induced electric current leads to an electric oscillating circuit in the first resonant circuit, so that a magnetic field is sent in the form of electromagnetic waves by the second inductance 10 in the area of the tube system 19. The first resonant circuit of the tube nozzle 2 is thus used for inductive coupling between the induction coil 11 of the respirator 4 and the tube system 19.

An inductance 8 acting as an induction coil 11 and a capacitance are connected by means of electric lines (not shown) in the tube system 19. Furthermore, an RFID semiconductor chip 17, which is supplied with electric energy by the electric oscillating circuit in the tube system 19 by means of electric lines 18, is integrated in the tube system 19. The tube nozzle 2 and the tube system 19 thus are RFID transponders each. Thus, signals or information can be sent to the tube system 19 and/or to the tube nozzle 2 and vice versa from the writing and/or reading module 5. The information or data may be, for example, information on the patient, on disinfection, on technical parameters or on other settings. The respirator 4 is coupled with various tube systems 19, so that it is necessary to transmit such special information of the tube system 19 to the respirator 4 for proper function. The transmission or sending of information or signals may take place, for example, by means of sending electromagnetic waves as a magnetic field or by means of a field attenuation of an electromagnetic field sent or by antiphase reflection of the field sent. The sending of information or signals may thus also take place by means of changing an electromagnetic sending field (not shown).

The RFID semiconductor chip 17 is integrated in the tube nozzle 2. The tube nozzle 2 can thus be checked after autoclaving operations (hot steam sterilization) without the additional presence of a tube system 19 or of a service transponder. A corresponding magnetic field is sent for this by the induction coil 11 in the respirator 4 to the tube nozzle 2. The RFID semiconductor chip 17 in the tube nozzle 2 can send a serial number or an identification code back to the respirator 4 based on the magnetic field sent. The writing and/or reading module 5 of the respirator 4 can interpret this sending of the identification code to mean that the tube nozzle 2 is in order, i.e., full operatability of the tube nozzle 2 continues to be guaranteed, for example, after autoclaving operations. If no identification code is sent back by the RFID semiconductor chip 17 in the tube nozzle 2 after the magnetic field has been sent by the induction coil 11 in the respirator 4, this can be interpreted by the writing and/or reading module 5 to mean that the tube nozzle 2 is no longer in order. This means that the operatability of the tube nozzle 2 is no longer fully guaranteed and it must be replaced after, for example, an autoclaving operation. This may be indicated, for example, by a corresponding lighting means at the respirator 4 (not shown). Furthermore, data or information on the compatibility between the tube nozzle 2 and a tube system 19 and/or the respirator 4 may be advantageously stored in the RFID semiconductor chip 17 of the tube nozzle 2. In addition, technical parameters, e.g., service data, concerning the number of autoclaving operations, may also be stored on the tube nozzle 2. This makes it possible, for example, to automatically replace a tube nozzle 2 after an existing certain number of autoclaving operations. The operatability of the tube nozzle 2 can thus be checked without the tube system 19, so that the operatability of the inductive coupling between the respirator 4 and the tube system 19 can thus preferably be checked as well.

On the whole, considerable advantages are associated with the coupling device 1 according to the present invention and the system 7 according to the present invention. An additional service transponder for checking the inductive coupling between the respirator 4 and the tube system 19 is no longer necessary in the system 7 because checking of the tube nozzle 2 is also possible without the tube system 19 due to the RFID semiconductor chip 17 being arranged in the tube nozzle 2.

While specific embodiments of the invention have been described in detail to illustrate the application of the principles of the invention, it will be understood that the invention may be embodied otherwise without departing from such principles.

LIST OF REFERENCE NUMBERS

1 Coupling device
2 Tube nozzle
3 Medical device
4 Respirator
5 Writing and/or reading module
6 Accessory
7 System
8 Inductance
9 First inductance
10 Second inductance
11 Induction coil
12 Capacitance
13 First capacitance
14 Second capacitance
15 Plate capacitor
16 Semiconductor chip
17 RFID semiconductor chip
18 Electric line
19 Tube system
20 First electric circuit
21 Second electric circuit

What is claimed is:

1. A coupling device for a medical device for a mechanical and electromagnetic coupling of the medical device, having a medical device inductance associated with the medical device, with an accessory, having an accessory inductance associated with the accessory, the coupling device comprising:

a mechanical coupling means for mechanically coupling the medical device with the accessory;

an electromagnetic coupling means for electromagnetic coupling the medical device with the accessory, the electromagnetic coupling means including an inductance, a capacitance and an electric line for forming an electric circuit as a resonant circuit for magnetically coupling the medical device inductance with the accessory inductance; and a semiconductor chip for storing and/or processing at least one piece of information and/or for sending and/or receiving at least one signal.

2. A coupling device in accordance with claim 1, wherein the semiconductor chip is an RFID semiconductor chip and/or the coupling device comprises an RFID transponder.

3. A coupling device in accordance with claim 1, wherein the medical device inductance is arranged in an area of the medical device and the accessory inductance is arranged in an area of the accessory.

4. A coupling device in accordance with claim 1, wherein the capacitance comprises two capacitances and the semiconductor chip is electrically connected to the electric circuit acting as a resonant circuit by means of said two capacitances to supply the semiconductor chip with electric energy.

5. A coupling device in accordance with claim 4, wherein the semiconductor chip, one said inductance and an electric line form a second electric circuit acting as a resonant circuit.

6. A coupling device in accordance with claim 1, wherein the coupling device comprises a tube nozzle.

7. A coupling device in accordance with claim 1, wherein the medical device is a respirator and/or the accessory is a tube system.

8. A medical system comprising:
a medical device with a medical device inductance for generating an electromagnetic field and a writing and/or reading module;
an accessory with an accessory inductance for generating an electromagnetic field and a semiconductor chip; and
a coupling device for mechanically and electromagnetically coupling the medical device with the accessory, the coupling device comprising a mechanical coupling means for mechanically coupling the medical device with the accessory, a coupling device inductance, a capacitance and an electric line to form an electric circuit as a resonant circuit for the electromagnetic coupling of the inductance at the medical device with the inductance at the accessory and with a semiconductor chip for storing and/or processing at least one piece of information and/or for sending and/or receiving at least one signal.

9. A system in accordance with claim 8, wherein:
the coupling device is a tube nozzle;
the medical device is a respirator; and
an operatability of the coupling device is detected by the medical device by means of the semiconductor chip in the coupling device.

10. A system in accordance with claim 8, wherein:
the accessory is a tube system; and
an operatability of a communication between the medical device and the accessory is detected by the medical device by means of the semiconductor chip in the coupling device.

11. A process for detecting a state of a coupling device, the process comprising the steps of:
providing a medical device with a medical device inductance for generating an electromagnetic field and a writing and/or reading module;
providing an accessory with an accessory inductance for generating an electromagnetic field, with an accessory capacitance and an accessory electric line providing an accessory resonant circuit as an accessory electric circuit with an accessory semiconductor chip;
providing a coupling device for mechanically and electromagnetically coupling the medical device with the accessory, the coupling device comprising a mechanical coupling means for mechanically coupling the medical device with the accessory, a coupling device inductance, a capacitance and an electric line to form an electric circuit as a resonant circuit for the electromagnetic coupling of the inductance at the medical device with the inductance at the accessory and with a semiconductor chip for storing and/or processing at least one piece of information and/or for sending and/or receiving at least one signal;
generating the magnetic field from the medical device;
inducing electric current in the resonant circuit by means of the energy from the magnetic field of the medical device;
generating the electromagnetic field from the coupling device by means of the resonant circuit thereof;
inducing electric current in the accessory resonant circuit in the accessory;
sending at least one piece of information and/or at least one signal from the medical device to the accessory and/or vice versa by means of the generated and induced electromagnetic field; and
storing and/or processing at least one piece of information and/or receiving and/or sending a signal from the semiconductor chip in the coupling device.

12. A process in accordance with claim 11, wherein the at least one piece of information and/or the at least one signal is transmitted in a wireless manner from the semiconductor chip with the resonant circuit in the coupling device to the medical device and/or vice versa by an electromagnetic field or by the electromagnetic field.

13. A process in accordance with claim 11, wherein after the magnetic field has been sent from the medical device, the coupling device sends at least one signal, especially with an identification code and/or with at least one piece of information, to the medical device and the sending of the at least one signal to the medical device is interpreted to mean that trouble-free communication between the medical device and the coupling device and/or the accessory is possible and/or the coupling device is operative.

14. A process in accordance with claim 11, wherein after the magnetic field has been sent from the medical device, the coupling device sends no signal to the medical device and the lack of sending of the signal to the medical device is interpreted to mean that trouble-free communication between the medical device and the coupling device and/or the accessory is not possible and/or the coupling device is not operative.

15. A process in accordance with claim 11, wherein:
the coupling device is a tube nozzle;
the medical device is a respirator; and
an operatability of the coupling device is detected by the medical device by means of the semiconductor chip in the coupling device.

16. A process in accordance with claim 15, wherein:
the accessory is a tube system; and
an operatability of a communication between the medical device and the accessory is detected by the medical device by means of the semiconductor chip in the coupling device.

* * * * *